(12) United States Patent
Stass

(10) Patent No.: US 7,205,009 B2
(45) Date of Patent: Apr. 17, 2007

(54) COMPOSITION FOR TREATING HAIR AND SCALP AND METHOD FOR PREPARING SAME

(76) Inventor: Dirk Stass, 178 Sugar Lake Road, Lumby, British Columbia (CA) V0E 2G1

( * ) Notice: Subject to any disclaimer, the term of this patent is extended or adjusted under 35 U.S.C. 154(b) by 0 days.

(21) Appl. No.: 11/291,828

(22) Filed: Dec. 2, 2005

(65) Prior Publication Data

US 2006/0120990 A1    Jun. 8, 2006

Related U.S. Application Data

(60) Provisional application No. 60/632,195, filed on Dec. 2, 2004.

(51) Int. Cl.
*A61K 36/38* (2006.01)

(52) U.S. Cl. ..................................... 424/730

(58) Field of Classification Search ............... None
See application file for complete search history.

(56) References Cited

U.S. PATENT DOCUMENTS

| | | | |
|---|---|---|---|
| 4,459,285 A | 7/1984 | Grollier et al. | |
| 4,569,839 A * | 2/1986 | Grollier et al. | ............ 424/74 |
| 4,581,230 A | 4/1986 | Grollier et al. | |
| 4,746,510 A | 5/1988 | Grollier et al. | |
| 4,767,618 A | 8/1988 | Grollier et al. | |
| 4,880,621 A | 11/1989 | Grollier et al. | |
| RE33,993 E | 7/1992 | Grollier et al. | |
| 5,133,958 A | 7/1992 | Stuckler | |
| 5,270,035 A | 12/1993 | Chimento | |
| 5,407,675 A | 4/1995 | Etemad-Moghadam | |
| 5,525,594 A * | 6/1996 | Gourvest et al. | ............ 514/25 |
| 5,641,480 A | 6/1997 | Vermeer | |
| 5,653,970 A | 8/1997 | Vermeer | |
| 5,972,345 A | 10/1999 | Chizick et al. | |
| 6,103,272 A | 8/2000 | Keeney | |
| 6,159,487 A | 12/2000 | Znaiden et al. | |
| 6,284,234 B1 | 9/2001 | Niemiec et al. | |
| 6,358,541 B1 | 3/2002 | Goodman | |
| 6,419,913 B1 | 7/2002 | Niemiec et al. | |
| 6,420,352 B1 | 7/2002 | Knowles | |
| 6,471,951 B1 * | 10/2002 | Nardolillo et al. | ............ 424/63 |
| 6,576,270 B2 | 6/2003 | Leko | |
| 6,620,410 B1 | 9/2003 | Cho et al. | |
| 6,740,317 B1 | 5/2004 | Cho et al. | |
| 6,762,158 B2 | 7/2004 | Lukenbach et al. | |
| 2002/0028257 A1 * | 3/2002 | Catalfo et al. | ............ 424/727 |
| 2002/0183297 A1 | 12/2002 | Niazi | |
| 2004/0096420 A1 | 5/2004 | Catalfo et al. | |
| 2004/0116539 A1 | 6/2004 | Biercevicz et al. | |

FOREIGN PATENT DOCUMENTS

RU       2008013 C1 *  2/1994

OTHER PUBLICATIONS

PDR for Herbal Medicines-First Edition. pp. 1212-1214, copyright 1998. Medical Economics Company.*

* cited by examiner

*Primary Examiner*—Christopher R. Tate
*Assistant Examiner*—Melenie McCormick
(74) *Attorney, Agent, or Firm*—Antony C. Edwards

(57) ABSTRACT

An herbal composition for the re-growth of human hair includes the combination of *hypercium perforatum, veronica beccabunga, veronica officinalis*, and *equisetum arvense* wherein the combination is infused in water and adapted to be applied to the scalp of a user.

20 Claims, No Drawings

COMPOSITION FOR TREATING HAIR AND SCALP AND METHOD FOR PREPARING SAME

CROSS REFERENCE TO RELATED APPLICATION

This application claims priority from United States Provisional Patent Application No. 60/632,195 filed Dec. 2, 2004 entitled Composition for Treating Hair and Scalp and Method for Preparing Same.

FIELD OF THE INVENTION

The present invention relates to the field of herbal remedies, and more particularly, it relates to an herbal hair and scalp formula.

BACKGROUND OF THE INVENTION

For many years, the pharmaceutical industry, the nutraceutical industry, and the cosmetic industry have been researching and developing compositions that will cure or prevent hair loss or promote hair growth. Androgenic alopecia, which is the most common type of hair loss, is usually associated with genetic factors that cause hair follicles on the top of the scalp to have an increased sensitivity to the hormone dihyrdotestosterone (DHT). The combination of testosterone present in the follicles with the enzyme 5 alpha reductase produced by the hair follicles produces DHT. Hair follicle receptors sensitive to DHT thereby respond to the presence of DHT which shrinks the hair follicles until they no longer produce visible hair, thereby beginning the process of hair loss. Other factors including physical and emotional stress, hormonal problems, medications, and underlying diseases such as thyroid problems and diabetes have been associated with causing hair loss as well.

There are surgical and non-surgical solutions to address the problem of hair loss. Surgical options include hair grafting, which involves removing small pieces of hair bearing scalp from the back and sides of the head and transplanting them into holes and slits on the top of the head. Scalp reduction is another surgical alternative which involves surgical removal of bald areas on the top of the scalp. The problem with surgical solutions is the cost associated with such procedures, the medical risks associated with surgery, and the time commitment required pre and post surgery for preparation and recovery.

With respect to non-surgical options, there are hair extensions which involve attaching synthetic or human hair to existing hair or scalp to give the appearance of a fuller head of hair. Hair extensions are typically weaved into existing hair or attached to the scalp by adhesives. Although hair extensions are a less intrusive and less costly way of addressing hair loss, hair extensions fail to cure or prevent hair loss or promote hair growth. Hair extensions merely mask the problem and fail to provide a solution that addresses the root of the hair loss problem. Furthermore, adhesives for attaching hair extensions may cause skin irritation and hair weaving may cause permanent hair loss at the attachment site due to prolonged tension.

Other non-surgical options for treating hair loss include a variety of pharmaceutical and nutraceutical topical and/or oral treatments that promote hair re-growth and/or prevent further hair loss. For example, topical minoxidil, commonly known as ROGAINE, causes hair growth when applied to the scalp and slows the rate of hair loss in some individuals by stimulating hair follicles. Finasteride, commonly known as PROPECIA is a drug that is taken orally to treat androgenic alopecia by blocking the formation of DHT. The problem with treating hair loss with pharmaceutical drugs is the potential side effects of such drugs. Minoxidil may cause low blood pressure, increase in heart rate, weight gain due to water retention, and the scalp may become inflamed. Finasteride may cause genital deformities in male infants, impotence, decreased libido, hives or rash, and swelling.

Nutraceutical or herbal remedies for hair loss typically focus on increasing blood supply to the scalp, removing sebum in the scalp to prevent clogging of the pores, and/or increasing nutrition to the hair root to reduce hair loss and promote hair growth. There are numerous herbal remedies for the treatment and prevention of hair loss available in the art that target specific suspected causes of hair loss. For example, there are a plurality of herbal remedies for treating hair loss that are directed to improving blood circulation to the scalp without regard to other bodily malaises that may be contributing to hair loss. None of the available remedies provide a comprehensive treatment of the numerous potential factors that may contribute to hair loss. As such, there exists a need to provide an herbal formula that attempts to correct a broad range of imbalances and problems that are typically associated with causing hair loss.

SUMMARY OF THE INVENTION

It is an object of the present invention to provide an herbal formula for treating hair and scalp and a method of preparing the same that is capable of providing a comprehensive treatment for a plurality of known and/or suspected causes of hair loss. The present invention retards and inhibits hair loss, and promotes hair re-growth. Inflammation associated with hair loss is reduced, the present invention providing for healing of the skin and scalp which results in hair re-growth and the corresponding cessation and prevention of hair loss.

In accordance with the present invention, there is provided a composition for treating hair and scalp comprising a combination of *hypercium perforatum, veronica beccabunga, veronica officinalis*, and *equisetum arvense* wherein the combination is infused in water and applied to the hair and scalp of a user. Preferably, the combination may further include one or more of *urtica dioica, menthe canadensis*, and *epilobium parviflorum*.

In an embodiment of the invention, the composition comprises between 150 to 250 grams of *hypercium perforatum,* 50 and 150 grams of *veronica beccabunga,* 50 and 150 grams of *veronica officinalis*, and 100 and 200 grams of *equisetum arvense* to produce between 150 to 250 litres of the composition according to the method described below. Preferably, 200 grams of *hypercium perforatum*, 100 grams of *veronica beccabunga,* 100 grams of *veronica officinalis*, and 150 grams of *equisetum arvense* is combined to produce 200 litres of the composition or 20 litres of 10:1 concentrate.

In another embodiment of the invention, the composition may further comprise between 100 and 200 grams of *urtica dioica*. In another embodiment of the invention, the composition may also comprise between 25 and 75 grams of *mentha canadensis*. In yet another embodiment of the invention, the composition may further comprise between 100 to 200 grams of *epilobium parviflorum*. Preferably, the composition further comprises a combination of 150 grams of *urtica dioica*, 50 grams of *menthe canadensis*, and 150 grams of *epilobium parviflorum* to produce about 200 litres of the composition.

The method of preparing the composition according to the present invention includes the steps of reducing each of the herbs in the combination such that the active ingredients of the herbs may be released. A first predetermined amount of water is then added to the reduced herb combination. The water and reduced herb combination is then brought to a boil for a predetermined period of time such that the herbs may infuse the water to produce a composition concentrate. The reduced herbs are then removed from the composition concentrate by conventional straining means and a second predetermined amount of water is added to the composition concentrate to form the composition. It is intended that the quantities of herbal ingredients set out herein described as resulting in 200 litres of the composition may be scaled according to their corresponding ratios (grams of a particular element:litres of water) to make correspondingly less or more of the composition.

In an embodiment of the invention, ten to twenty litres of distilled cold water is added to the reduced herbs to produce the composition concentrate. Preferably, after ten minutes of infusion, the composition concentrate is filtered and a second amount of distilled cold water is added to the filtered composition concentrate to produce the approximately 200 litres of the composition. In an embodiment of the invention, a preservative may be added to the composition.

DETAILED DESCRIPTION OF EMBODIMENTS OF THE INVENTION

The composition for treating hair and scalp according to the present invention includes the following herbs combined in a first embodiment: *hypercium perforatum, veronica beccabunga, veronica officinalis*, and *equisetum arvense*. In further embodiments of the invention, the composition may further include *urtica dioica, menthe canadensis*, and *epilobium parviflorum*. The composition may include all the above listed herbs.

*Hypercium perforatum* is commonly known as St. John's Wort. *Hypercium perforatum* is a flowering plant known for its antidepressant properties and has been correlated with relieving anxiety, apathy, sleep disturbances, insomnia, and feelings of worthlessness. *Hypercium perforatum* reportedly balances the nervous system by injecting oxygen into cells which helps to elevate mood. Because one of the factors known to be associated with hair loss is emotional and physical stress, *hypercium perforatum* is a main ingredient in the present invention. In the present invention, between 150 to 250 grams of *hypercium perforatum* is used to produce between approximately 200 litres of the composition according to the method described below. It is believed that *hypercium perforatum* has no known interactions with prescription drugs or alcohol and that the only known side effect in humans includes photosensitivity.

*Veronica beccabunga*, commonly known as Brooklime, is an herb known for its alterative, antioxidant, and diuretic properties and is usually recommended for treating impurity of the blood. *Veronica beccabunga* has also been used as an antiscorbutic and for treating affections of the skin. In the present invention, between 50 and 150 grams of *veronica beccabunga* is used to produce between approximately 200 litres of the composition. The diuretic property of *veronica beccabunga* helps to lower blood pressure, purify blood by encouraging the elimination of toxins from the body, and cleanse the urinary system and the alterative property helps restore general health to the body and increase oxygen to the blood.

*Veronica officinalis*, also known as Common Speedwell, is an herbaceous plant that has long been used medicinally to treat coughs, stomach and urinary disorders, and rheumatism. *Veronica officinalis* has antioxidant properties and is an expectorant, alterative, tonic and diuretic. In the present invention, between 50 and 150 grams of *veronica officinalis* is used to produce between approximately 200 litres of the composition. The diuretic property of *veronica officinalis* helps to lower blood pressure, purify blood, and cleanse the urinary system and the expectorant property promotes elimination of matter from the respiratory tract. The alterative and tonic properties of *veronica officinalis* facilitate restoration of digestive, respiratory and urinary systems and increase oxygen to the blood.

*Equisetum arvense* is an herbaceous plant commonly known as Field Horsetail. *Equisetum arvense* has generally been recommended for treating conditions affecting the parathyroid glands, kidney, and bladder. *Equisetum arvense* is known to have antioxidant properties and be rich in minerals which play a vital role in regulating many body functions, including nerve response, muscle contraction, metabolism, and regulating electrolyte balance and hormonal production. In the present invention, between 100 and 200 grams of *equisetum arvense* is used to produce between approximately 200 litres of the composition. The mineralizing property of *equisetum arvense* regulates the function of the parathyroid glands which affect the calcium and phosphorus levels in blood and balances hormone and electrolyte levels in the blood.

In a second embodiment of the invention, the composition may also include *urtica dioica* which is a tropical plant commonly known as Nettle or Stinging Nettle. Internally, *urtica dioica* has been traditionally used as a diuretic, to build blood, and for treating arthritis and rheumatism, diabetes, urinary disorders, respiratory problems, and dermatological problems. Externally, *urtica dioica* has been used as a remedy to cure dandruff and oily hair and to improve the appearance of hair. In the present invention, between 100 and 200 grams of *urtica dioica* may be added to produce between approximately 200 litres of the composition. The anti-inflammatory property of *urtica dioica* that functions at a hormonal level has been associated with interfering or blocking hormone related chemical processes in the body, including the activity of DHT. *Urtica dioica* is also known to be a high source of iron.

In a third embodiment of the invention, the composition may further include *mentha canadensis* which is an herbaceous plant commonly known as Mint. *Mentha canadensis* is known to alleviate and treat stomach pain, indigestion, and other digestive disorders. In the present invention, between 25 and 75 grams of *mentha canadensis* may be added to produce between approximately 200 litres of the composition. *Mentha canadensis* acts as a catalyst to emphasize the effects of the herbs, particularly the oxygen inducing and antioxidant properties of *hypercium perforatum, veronica beccabunga, veronica officinalis*, and *equisetum arvense*. The curative property of *mentha canadensis* on the digestive system assists in alleviating any digestive malaise that may contribute to any imbalance in the body. Because of the antiseptic property of *mentha canadensis* and the astringent property of *veronica officinalis, urtica dioica*, and *equisetum arvense*, the composition may also be used treat wounds such as cuts and scrapes and other similar injuries.

In a fourth embodiment of the invention, the composition may further include *epilobium parviflorum* which is a flowering herb commonly known as Small-flowered Hairy Willow-herb. *Epilobium parviflorum* has been used to treat prostate disorders as it is suspected that *epilobium parviflorum* inhibits the activity of 5-alpha-reductase, the enzyme responsible for the production of DHT. In the present invention, between 100 and 200 grams of *epilobium parviflorum* may be added to produce between approximately 200 litres of the composition.

The method of preparing the composition includes the steps of grinding, pulverizing, or otherwise reducing each of the herbs such that the active ingredients in the herbs may be released. Preferably, the herbs are dried and coarsely ground although fresh herbs maybe used. A predetermined amount of water is then added to the combination of herbs and brought to a boil such that the herbs may infuse the water to produce a composition concentrate. In an embodiment of the invention, distilled cold water is added to the combination of herbs. Preferably, between ten and twenty litres of water is added to the fourth embodiment combination of herbs which includes 200 grams of *hypercium perforatum*, 100 grams of *veronica beccabunga*, 100 grams of *veronica officinalis*, 150 grams of *equisetum arvense*, 150 grams of *urtica dioica*, 50 grams of *menthe canadensis*, and 150 grams of *epilobium parviflorum*.

After the herbs infuse the water for a predetermined amount of time, the composition concentrate is strained to separate the herbs from the composition concentrate. In an embodiment of the invention, the combination of herbs may infuse the water between five to fifteen minutes. Preferably, the composition concentrate is strained after a period of ten minutes. The combination of herbs may be separated from the composition concentrate by using conventional strains or sieves. Preferably, a filter pump is used to tightly filter the composition concentrate to ensure that most of the sediment is removed from the composition concentrate. A predetermined amount of water is then added to the composition concentrate to produce the composition. Preferably, approximately 180 litres of distilled cold water is added to the approximately 20 litres of composition concentrate to produce the 200 litres of the composition. In an embodiment of the invention, a preservative such as potassium sorbate may be added to the composition.

The composition may then be applied to the hair and scalp of the user to prevent further hair loss and to promote hair re-growth. The composition may be applied directly or sprayed onto the hair or scalp two to three times daily. The hair and scalp may be wet or dry. Preferably, the composition is massaged into the hair and scalp and let to dry without rinsing.

In testing the composition on one test subject, the combination of herbs of the fourth embodiment was applied twice daily to the scalp of the test subject. At the commencement of testing, hair was noticeably missing over a significant area around the top of the scalp of the test subject. Over the course of two to three months, re-growth of fine hairs over the affected area was observed and after four to five months, a considerable amount of mature hair over the affected area was observed. In the case of the test subject, after four months, mature hair re-growth covered approximately 85% of the hair loss area observed at the commencement of testing.

Although not wishing to be bound to any particular theory of operation, it is applicant's opinion that the synergy between the antioxidant and oxygen inducing properties of the combination of herbs in the composition of the first embodiment encourages hair re-growth. The increase in oxygen to the cellular structure of the scalp and the neutralizing of free radicals in the body to prevent the oxidation process thereby heals the hypodermis of the scalp and promotes hair re-growth.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims which are intended to include within their scope lesser or greater quantities of the composition so long as the respective ratios of amount (grams) of herbs and water (litres) are maintained, for example as expressed in percentages by weight of the total weight of herbs employed or infused in a particular volume of water.

What is claimed is:

1. A composition for the re-growth of human hair comprising a herbal combination of *hypercium perforatum*, *veronica beccabunga*, *veronica officinalis*, and *equisetum arvense*, wherein the herbal combination is infused in water at a ratio of herb to water of between approximately 150 to 250 grams of said *hypercium perforatum*, between approximately 50 to 150 grams of said *veronica beccabunga*, between approximately 50 to 150 grams of said *veronica officinalis*, and between approximately 100 to 200 grams of said *equisetum arvense* per 175 to 225 liters of water, and wherein the composition is adapted to be applied to the scalp of a user.

2. The composition of claim 1 wherein the herbal combination further comprises one or more of *urtica dioica*, *mentha canadensis*, and *epilobium parviflorum*.

3. The composition of claim 1 wherein the herbal combination is infused in water at a ratio of herb to water of approximately 200 grams of said *hypercium perforatum*, approximately 100 grams of said *veronica beccabunga*, approximately 100 grams of said *veronica officinalis*, and approximately 150 grams of said *equisetum arvense* per 200 liters of water.

4. The composition of claim 3 further comprising infusing between approximately 100 to 200 grams of *urtica dioica* in said water.

5. The composition of claim 3 further comprising infusing between approximately 25 to 75 grams of *mentha canadensis* in said water.

6. The composition of claim 3 further comprising infusing between approximately 100 to 200 grams of *epilobium parviflorum* in said water.

7. The composition of claim 3 further comprising infusing approximately 150 grams of *urtica dioica*, approximately 50 grams of *mentha canadensis*, and approximately 150 grams of *epilobium parviflorum* in said water.

8. A method for preparing a herbal composition for the re-growth of human hair, the method comprising infusing a herbal combination of *hypercium perforatum, veronica beccabunga, veronica officinalis*, and *equisetum arvense* in water wherein the herbal combination is infused in water at a herb to water ratio of between approximately 150 to 250 grams of said *hypercium perforatum*, between approximately 50 to 150 grams of said *veronica beccabunga*, between approximately 50 to 150 grams of said *veronica officinalis*, and between approximately 100 to 200 grams of said *equisetum arvense* per 175 to 225 liters of water.

9. The method of claim 8 wherein the herbal combination further comprises one or more of *urtica dioica, mentha canadensis*, and *epilobium parviflorum*.

10. The method of claim 8 wherein the herbal combination is infused in water at a herb to water ratio of approximately 200 grams of said *hypericum perforatum*, approximately 100 grams of said *veronica beccabunga*, approximately 100 grams of said *veronica officinalis*, and approximately 150 grams of said *equisetum arvense* per 200 liters of water.

11. The method of claim 10 further comprising infusing between approximately 100 to 200 grams of *urtica dioica* in said water.

12. The method of claim 10 further comprising infusing between approximately 25 to 75 grams of *mentha canadensis* in said water.

13. The method of claim 10 further comprising infusing between approximately 100 to 200 grams of *epilobium parviflorum* in said water.

14. The method of claim 10 further comprising infusing approximately 150 grams of *urtica dioica*, approximately 50 grams of *mentha canadensis*, and approximately 150 grams of *epilobium parviflorum* in said water.

15. The method of claim 8 further comprising the steps of:
  a) reducing each of said herbs of the herbal combination;
  b) adding a first predetermined amount of water to said reduced herbs;
  c) boiling said first predetermined amount of water and said reduced herbs for a predetermined period of time such that said herbs infuse said water to produce a concentrate of said herbal composition;
  d) removing said reduced herbs from said concentrate by straining; and
  e) adding a second predetermined amount of water to said concentrate to form said herbal composition.

16. The method of claim 15 wherein said first predetermined amount of water is approximately 20 liters of distilled cold water and wherein said second predetermined amount of water is approximately 180 liters of distilled cold water.

17. The method of claim 8 further comprising the steps of:
  a) reducing each of said herbs of the herbal combination;
  b) adding a first predetermined amount of water to said reduced herbs;
  c) boiling said first predetermined amount of water and said reduced herbs for a predetermined period of time such that said herbs infuse said water to produce a concentrate of said herbal composition;
  d) removing said reduced herbs from said concentrate by straining; and
  e) adding a second predetermined amount of water to said concentrate to form said herbal composition.

18. The method of claim 17 wherein said first predetermined amount of water is approximately 20 liters of distilled cold water and wherein said second predetermined amount of water is approximately 180 liters of distilled cold water.

19. A method for the re-growth of human hair, comprising applying the herbal composition made by the method of any one of claims 8, 10, 15 and 17 to the scalp of a subject in need thereof.

20. A method for the re-growth of human hair, comprising applying the composition of any one of claims 1, 2 and 3–7 to the scalp of a subject in need thereof.

\* \* \* \* \*